United States Patent [19]

Zhou et al.

[11] Patent Number: 5,688,676
[45] Date of Patent: *Nov. 18, 1997

[54] IN VITRO PACKAGING OF ADENO-ASSOCIATED VIRUS DNA

[75] Inventors: Xiaohuai Zhou; Nicholas Muzyczka; Sergei Zolotukhin, all of Gainesville, Fla.; Tiehua Ni, Malden, Mass.

[73] Assignee: Research Foundation of State University of New York, Stony Brook, N.Y.

[ * ] Notice: The term of this patent shall not extend beyond the expiration date of Pat. No. 5,677,158.

[21] Appl. No.: 477,511

[22] Filed: Jun. 7, 1995

[51] Int. Cl.$^6$ .......................... C12P 21/06; C12N 15/64; C12N 15/00; C12N 7/00
[52] U.S. Cl. .................... 435/172.3; 435/172.1; 435/635.1; 435/320.1
[58] Field of Search .............................. 435/320.1, 172.1, 435/172.3, 235.1, 91.2, 69.1, 91.4

[56] References Cited

U.S. PATENT DOCUMENTS

| | | | |
|---|---|---|---|
| 4,797,368 | 1/1989 | Carter et al. | 435/320.1 |
| 5,139,941 | 8/1992 | Muzyczka et al. | 435/172.3 |

OTHER PUBLICATIONS

Kotin et al., Prospects for the Use of Adeno–Associated Virus as a Vector for Human Gene Therapy, Hum. Gene Therapy, V. 5, pp. 793–801, 1994.

Ni et al., In Vitro Replication of Adeno–Associated Virus DNA, J. Virol., V. 68:2, pp. 1129, 1994.

Chejannovsky and Carter, "Replication of a Human Parvovirus Nonsense Mutant in Mammalian Cells Containing an Inducible Amber Suppressor", *Virology*, 171:239–247 (1989).

Hermonant and Muzyczka, "Use of Adeno–Associated Virus as a Mammalian DNA Cloning Vector: Transduction of Neomycin Resistance Into Mammalian Tissue Culture Cells", *Proc. Natl. Acad., Sci. U.S.A.*, 81:6466–6470 (Oct. 1984).

Lebkowski et al., "Adeno–Associated Virus: a Vector System for Efficient Introduction and Integration of DNA Into a Variety of Mammalian Cell Types" *Molecular and Cellular Biology*, 8(10):3988–3996 (Oct. 1988).

McLaughlin et al., "Adeno–Associated Virus General Transduction Vectors: Analysis of Proviral Structures", *J. of Virology*, 62(6):1963–1973 (Jun. 1988).

Mendelson et al., "Expression and Rescue of a Nonselected Marker from an Integrated AAV Vector", *Virology*, 166:154–165 (1988).

Molla et al., "Cell Free, De Novo Synthesis of Poliovirus", *Science*, 254:1647–1651 (Dec. 1991).

Samulski et al., "Helper–Free Stocks of Recombinant Adeno–Associated Viruses: Normal Intergratin Does Not Require Viral Gene Expression", *Journal of Virology*, 63(9)3822–3828 (Sep. 1989).

Tratschin et al., "Adeno–Associated Virus Vector for High-Frequency Integration, Expression, and Rescue of Genes in Mammalian Cells", *Molecular Cellular Biology*, 5(11):3251–3260 (Nov. 1985).

Vincent et al., "Replication and Packaging of HIV Envelope Genes in a Novel Adeno–Associated Virus Vector System" *Vaccines*, 90:353–359 (1990).

*Primary Examiner*—David Guzo
*Assistant Examiner*—Andrew Wang

[57] ABSTRACT

A method for in vitro packaging of adeno-associated viral particles is described. The procedure involves the preparation of cell-free extracts containing all the essential components for packaging. Homogeneous purified substrate DNA for packaging may be prepared separately. The in vitro packaged AAV particles are useful in transduction of mammalian cells and for gene therapy in animals. In one described method, the DNA packaged into AAV particles is not limited by the size constraints characteristic of in vivo packaged AAV particles.

19 Claims, 4 Drawing Sheets

IN VITRO PACKAGING OF ADENO-ASSOCIATED VIRUS DNA

ACKNOWLEDGEMENTS

This invention was supported in part by grants from the National Institute of General Medical Sciences (RO1 GM3572302) and the National Heart, Blood, and Lung Institute (RO1 HL/DK50257). The U.S. Government may have rights in this invention.

INTRODUCTION

Technical Field

This invention relates to certain mammalian transduction vectors and methods for production and use of in vitro encapsidated mammalian transduction vectors.

Background

Adeno-associated virus (AAV) belongs to the family Parvoviridae (Muzyczka, N., Current Topics in Microbiology and Immunology 158:97–129 1992). The parvovirus virion is composed of three structural proteins and a linear, single-stranded (ss) DNA genome. The particle has icosahedral symmetry and a diameter of 18–26 nm. Five serotypes of AAV have been identified but the most extensively characterized is AAV-2. The complete nucleotide sequence of AAV-2 has been reported (Srivastava et al., J. Virol. 45:555–564 1983) and contains 4680 bases. The AAV genome contains terminal inverted repeats (TR) of 145 bases.

At least three regions have been identified in the AAV genome by mutation studies. The rep region encodes four proteins that are required for AAV DNA replication and/or rescue. Rep proteins consist of four overlapping polypeptides: Rep78, Rep68, Rep52 and Rep40. The cap region appears to encode the AAV capsial proteins; routants in these regions are capable of DNA replication but do not form infectious particles. Mutation studies have shown that the inverted terminal repeats are required in cis for DNA replication.

The three capsid proteins of AAV—VP1, VP2, and VP3—have molecular weights of 90, 72, and 62 kDa and are present in the virion at a ratio of 1:1:10. Genetic study shows that VP2 and VP3 by themselves can encapsidate progeny DNA (Hermonat et al 1984 J. Virol. 51:329–333; Tratschin et al 1984 J. Virol. 51:611–619). However, virion particles lacking VP1 are less infectious than those with a full complement of capsid proteins. Parvovirus structural proteins including those of AAV, B19, and Aleutian disease virus expressed in insect cells are able to assemble into empty capsids (Ruffing et al. 1992 J. Virol. 66:6922–6930, 1992; Brown et al, 1991 J. Virol. 65:2702–2706; Christensen et al. 1993 J. Virol. 67:229–238). Results on the subcellular distribution of AAV capsid proteins suggest that the subunits must form complexes for efficient nuclear accumulation and subsequent particle assembly (Wistuba et al 1995 in press).

AAV can be propagated either as an integrated provirus or by lytic infection (Atchison et al. 1965 Science 149:754–756; Hoggan et al. 1972 Proceedings of the Fourth Lepetite Colloquium, Cocoyac, Mexico, North-Holland, Amsterdam, pp. 243–249). The ability to form a latent infection appears to be an integral part of the AAV life cycle. Except under special circumstances (Yacobson et al. 1987 J. Virol. 61:972–981; Schlehofer et al. 1986 Virology 152:110–117; Yalkinoglu et al. 1988 Cancer Res. 48:3123–3125), AAV requires the presence of a helper virus to initiate a productive viral infection. Members of either the herpes or adenovirus families can provide the necessary helper functions (Atchison et al. 1965 Science 149: 754–756; Melnick 1965 J. Bacteriol 90:271–274; McPherson 1985 Virology 147:217–222) and vaccinia virus can provide at least partial helper function (Schlehofer et al. 1986 Virology 152:110–117). In the absence of a helper virus, AAV produces no progeny virus but instead integrates into a host chromosome to form a provirus (Hoggan et al. 1972; Berns et al. 1975 Virology 68:556–560; Handa et al. 1977 Virology 82:84–92; Cheung et al. 1980 J. Virol. 33:739–748). With rare exceptions, AAV proviruses appear to be stable. However, if a cell line that is carrying an AAV provirus is subsequently superinfected with a helper virus, the AAV genome is excised and proceeds through a normal productive infection (Hoggan et al. 1972; Cheung et al. 1980 J. Virol. 33:739–748). This ability to establish a latent infection which can later be rescued appears to be a mechanism for ensuring the survival of AAV in the absence of a helper virus.

In vivo assembly of infectious AAV virion requires the presence of the inverted terminal repeats on the packaged DNA suggesting that the signal for packaging in vivo is located within the TR sequences (Samulski et al. 1989 J. Virol. 63:3822–3828; McLaughlin et al. 1988 J. Virol. 62:1963–1973). Genomic size exceeding 110% of wild type AAV leads to low efficiency of encapsidation. Kinetic study on AAV assembly in vivo has revealed that empty capsids are produced before the appearance of full particles (Myers and Carter, 1980 J. Virol. 102:71–82). It has been suggested that progeny DNA is packaged into preformed capsids in the absence of concomitant DNA replication. Alternatively, a model for packaging of Aleutian disease virus DNA suggests that encapsidation is initiated by interaction of the progeny DNA with empty viral capsids followed by displacement synthesis and eventually packaging of the DNA (Willwand and Kaaden, 1980 J. Virol. 64:1598–1605.

The use of AAV as a viral transduction vector was first demonstrated by Hermonat and Muzyczka (Proc. Natl Acad. Sci. 81:6466–6470 1984). The AAV capsid gene was deleted between map positions 52 and 92 to make the vector dl52-91, and the bacterial neomycin resistance gene under the control of the SV40 early promoter was inserted. A dl52-91/neo virus stock was obtained by transfecting the recombinant plasmid into human cells that had been infected with adenovirus. The missing capsid proteins were supplied by co-transfecting with a plasmid containing wild type cap genes. This approach generated dl51-91/neo virus stocks that contained up to $10^6$ infectious units/ml (Hermonat et al. 1984 J. Virol., 51:329–333). The transduction frequency of these stocks was approximately the same as the integration frequency for wild type virus, 0.5%–5.0% (Laughlin et al. 1986 J. Virol. 60:515–524 (1986); Handa et al. 1977 Virology 82:84–92). Other AAV vectors containing the AAV TR sequences and varying amounts of non-repeated AAV sequences have been demonstrated to be capable of efficiently transducing foreign DNA into human cells (McLaughlin et al. 1988 J. Virol. 62:1963–1973; Samulski et al. 1987 J. Virol. 61:3096–3101; Samulski et al. 1989 J. Virol. 63:3822–3828).

One of the difficulties in using rAAV transduction vectors has been the awkward procedure required for growing a recombinant virus stock. The growth of a recombinant stock requires the presence of both AAV and helper virus genes and the recombinant viral stock that is produced often contains both adenovirus and wild type AAV virus particles as contaminants. The use of a wild type AAV infectious plasmid to supply the AAV Rep and cap gene products in trans produces stocks with unacceptably high levels of wild type AAV virus, approximately 10:1 wild type to recombinant (Hermonat and Muzyczka, 1984; McLaughlin et al., 1988; Tratschin et al. 1985 Mol. Cell Biol. 5:3251:3260; Lebkowski et al. 1988 Mol. Cell Biol. 8:3988–3996; Vincent et al. 1988 Vaccine 90:353–359). For reasons that are not clear there is a strong bias toward amplification of the wild type virus. The same is true when a recombinant viral stock is amplified by complementation with wild type AAV virus.

Relevant Literature

Several strategies have been tried to reduce the level of wild type AAV virus in recombinant stocks. Hermonat and Muzyczka (1984) inserted a 2.5 kb fragment of lambda bacteriophage DNA into a nonessential region of the wild type AAV plasmid to produce a recombinant genome, ins96λ/M, which could replicate and supply all of the AAV gene products in trans but was itself too large to be packaged. Recombinant titers of $10^5$–$10^6$/ml could be obtained but the stocks were contaminated with wild type virus at the level of 5%–10% (Hermonat and Muzyczka 1984 Proc. Nat'l Acad. Sci. USA 91:6466–6470; McLaughlin et al. 1988 J. Virol. 62:1963–1973). The contaminating wild type AAV virus was apparently the result of recombination between the complementing helper plasmid, ins96λ/M, and the AAV vector sequences. Several laboratories have tried to use complementing AAV plasmids which are missing portions of the terminal repeats or contain rep mutations and, therefore, are incapable of being packaged (Tratschin et al. 1985 Mol. Cell Biol. 5:3251–3260; Lebkowski et al. 1988 Mol. Cell Biol. 8:3988–3996. This approach also produces significant levels of wild type contamination (1%–50%), presumably due to homologous recombination between overlapping portions of the rAAV and the complementing plasmids. In addition, the titers of the recombinant stocks are low ($10^2$–$10^3$/ml).

Samulski et al. (1989) constructed a complementing plasmid (pAAV/Ad) in which there were no homologous sequences between the recombinant AAV genome and the complementing helper AAV plasmid. This plasmid consisted of the AAV coding sequences flanked by the adenovirus 5 terminal repeats. The adenovirus termini apparently allowed the complementing AAV plasmid to undergo limited amplification after transfection into adenovirus-infected cells by the mechanism normally used for adenovirus DNA replication. The pAAV/Ad complementing plasmid produced recombinant virus titers of $10^4$–$10^5$/ml with no detectable wild type AAV contamination (Samulski et al. 1989 J. Virol. 63:3822–3828).

Vincent et al. (Vaccine 90:353–359 1990) isolated several HeLa cell lines which contained integrated copies of the AAV genome that were missing the terminal repeats. The absence of the terminal repeats prevented the rescue and packaging of the integrated AAV sequences when the cells were superinfected with adenovirus. One of the lines (HA25a) was capable of generating recombinant stocks with titers of $10^3$–$10^4$/ml. The low virus titers produced were apparently due to the low copy number of the wild type AAV genes in the packaging cell line. Mendelson et al. (Virology 166:154–165 1988) also isolated several cell lines which constitutively expressed the AAV Rep proteins.

Chejanovsky and Carter (Virology 171:239–247 1989) have reported the isolation of an amber mutant (pNTC3) in the AAV Rep gene. The mutation could be efficiently suppressed by growing it on a monkey cell line containing an inducible human serine tRNA amber suppressor. The virus titers obtained were $10^7$–$10^8$/ml (approximately 10% of the wild type liters obtained with the same monkey lines) but the reversion frequency of the amber mutation was approximately $10^{-5}$, thus generating unacceptable levels of contamination with wtAAV.

The current method for growing rAAV stocks is that devised by Hermonat and Muzyczka (1984) modified by using the pAAV/Ad described by Samulski et al. (1989) or by using a helper AAV plasmid with no AAV or adenovirus terminal sequences. These methods generate rAAV titers of approximately $10^6$/ml and may still contain detectable amounts of wtAAV. In addition, rAAV prepared in this way contains significant adenovirus contamination as well as contamination with adventitious viruses that are present in the host cell line. All of these difficulties could be solved by development of an in vitro packaging system for AAV. No in vitro packaging systems for mammalian DNA viruses has been described although Molla et al. (Science 254:1647–1651, 1991) have reported an in vitro packaging system for polio virus, an RNA virus.

SUMMARY OF THE INVENTION

It is an object of the present invention to provide a method for packaging a DNA substrate in an in vitro reaction to produce adeno-associated virus (AAV) particles capable of transduction of mammalian cells. It is a further object of the present invention to provide a method for producing cell-free extracts that are useful for in vitro packaging of DNA substrates into AAV particles that are capable of transduction. In vitro packaged AAV particles and methods for their use in transduction of mammalian cells are also provided.

These and other objects of the present invention as will hereinafter become readily apparent are accomplished by providing a method for packaging a DNA substrate into an AAV capsid in vitro to produce a viral particle or a recombinant viral particle that is capable of transferring the packaged DNA substrate to a recipient mammalian cell resulting in expression or function of the substrate DNA or some part of the substrate DNA in the recipient cell. In particular, the method of the present invention comprises (a) transfecting a mammalian cell culture permissive for AAV replication with a dAAV vector containing AAV capsid and Rep gene coding sequences; (b) infecting the cell culture with a helper virus; (c) preparing an extract from the transfected cell culture; (d) combining said extract with a DNA substrate; and, (e) incubating said extract under conditions to promote packaging of the substrate DNA. In more particular embodiments, the method of the present invention comprises additionally the step of heating the packaged extract at elevated temperatures and optionally the step of extracting the packaged extract with chloroform.

In other embodiments the present invention provides in vitro packaged AAV particles capable of transduction of recipient mammalian cells. In one such embodiment, the substrate DNA packaged into the AAV particles is not restricted by size and sequence constraints typical of previous rAAV vectors made by in vivo packaging methods.

The present invention also provides a method for transferring substrate DNA to recipient mammalian cells using the in vitro packaged AAV particles and a method for preparing a composition which is capable of carrying out the packaging of substrate DNA into AAV particles in vitro.

In order that the present invention may be better understood, the following definitions are provided.

helper virus: a virus such as adenovirus, herpesvirus, cytomegalovirus, Epstein-Barr virus, or vaccinia virus, which when infected into an appropriate eukaryotic cell, allows a productive AAV infection to occur.

helper AAV DNA: AAV DNA sequences used to provide AAV functions in trans to a recombinant AAV which lacks the functions essential for AAV replication and/or in vivo packaging.

rAAV: recombinant AAV; DNA molecule containing some AAV sequences, usually at a minimum the inverted terminal repeats or the double-D sequences described in WO 9413788, and some foreign (that is, non-AAV) DNA dAAV: deficient AAV; for purposes of this application dAAVs contain the Rep and capsid coding regions of AAV but lack intact inverted terminal repeats making them incapable of being packaged in vivo.

AAV particles: infectious particles produced by in vivo or in vitro packaging of DNA into a AAV capsid, the DNA packaged may be either wt AAV genome or an rAAV AAV(TRLacZ): AAV particles in which the packaged DNA contains TRLacZ (AAV terminal repeats and the LacZ coding sequence under control of the CMV promoter)

Transduction: the transfer of a gene(s) to a cell by means of a virus particle such that the gene is expressed in the cell Transfection: the transfer of DNA to a cells by any other physical or chemical method.

BRIEF DESCRIPTION OF THE DRAWINGS

The present invention will be better understood by reference to the following detailed description of the specific embodiments when considered in combination with the drawings that form part of the present application, wherein.

DESCRIPTION OF SPECIFIC EMBODIMENTS

Figure 1:
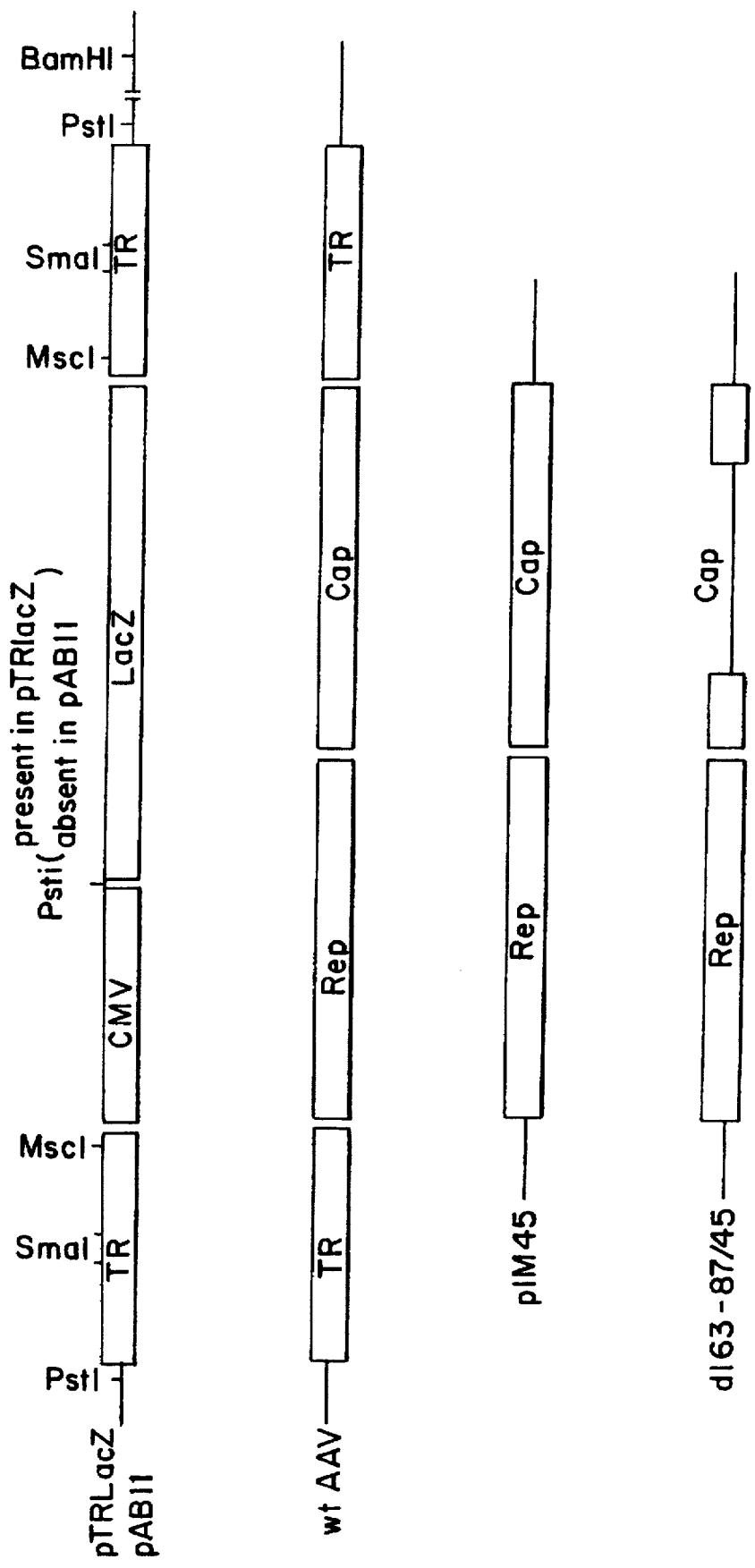
FIG. 1. Diagrams of pTRLacZ, pAB11, wild type AAV, pIM45, and d163-87/45. Cleavage sites of certain restriction endonucleases in pTRLacZ and pAB11 are shown. These restriction fragments were used as substrates for in vitro packaging experiments described in Table II. The diagram also illustrates the position of the capsid gene deletion in d163-87/45. pTRLacZ and pAB11 (Goodman et al. 1994 Blood 84:1492-1500) are rAAV plasmids containing the LacZ coding sequence under the control of the CMV early promoter and the SV40 early polyadenylation signals (not shown). pAB11 differs from pTRLacZ in that it is missing a PstI site near the junction of the CMV sequence and the LacZ gene and contains a nuclear localization signal in the LacZ coding sequence. Both plasmids contain no more AAV sequence than the 145 bp inverted repeat sequences. d163-87/45 contains a deletion of the region indicated by the dotted line. Neither pIM45 nor d163-87/45 have any homologous sequence with pTRLacZ or pAB11. Neither pIM45 nor d163-87/45 contain any AAV TR sequences.

Recombinant AAV vectors have several features that make them attractive candidates for human gene therapy. First, the cloning capacity of 5 kb can accommodate a variety of cDNAs. Second, the frequency of transduction in human cells is high. So far, no human cell line or tissue has been shown to be resistant to AAV transduction. Third, no disease has been associated with AAV in either human or animal populations. In addition, because rAAV vectors generally require two different helper viral genomes in order to propagate, there is an inherent limit to the natural spread of an AAV vector. In addition, if a proviral cell is superinfected with adenovirus, a Rep⁻ AAV provirus is incapable of DNA replication unless a wild type AAV genome is also supplied (McLaughlin et al. 1988 J. Virol. 62:1963–1973 (1988)). Individuals carrying an AAV provirus can be protected from adenovirus infection by vaccination. Fourth, AAV proviruses appear to be stable. Fifth, in the absence of the Rep gene, the AAV terminal repeats appears to be transcriptionally neutral. Thus, AAV vectors may be useful when it is essential to have foreign genes under the control of their own enhancer and promoter elements. Finally, there is no superinfection immunity for AAV vectors. A cell line can be transduced multiple times with several different AAV vectors (Lebkowski et al. 1988 Mol. Cell Biol. 8:3988–3996; McLaughlin et al. 1988 J. Virol. 62:1963–1973).

Previous methods for the production of infectious viral stocks of recombinant AAV (rAAV) vectors have employed packaging of the rAAV genomes in vivo during the course of a productive infection. Productive infection and in vivo packaging of rAAV requires the presence of a helper virus, like adenovirus, as well as complementation with essential AAV functions which have been deleted from the rAAV genome. The result is that rAAV viral stocks produced in vivo can contain significant levels of helper virus and of wild type (wt) AAV. In addition, the titer of the rAAV particles packaged in vivo is typically significantly lower than that obtained for wt AAV. Furthermore, any AAV vectors prepared in cell culture are subject to contamination with adventitious viruses that may be present in the cells used for growing the rAAV.

The present invention overcomes these difficulties by providing a method of packaging the rAAV genome in vitro. By in vitro is meant occurring in other than an intracellular millieu. The in vitro packaging may be carried out under conditions where the rAAV genome is the only DNA present and therefore contamination of the in vitro packaged rAAV viral stock with wt AAV or helper virus is eliminated. In addition, in one embodiment, the method of the present invention allows the production of AAV particles capable of transduction of substrate DNA that is at least two-fold larger than the wt AAV genome and does not require the presence of AAV TR sequences on the substrate DNA.

In the method of the present invention, a packaging component cellular extract (PCCE) is prepared from host cells transfected with a deficient AAV (dAAV) vector and infected with a helper virus. The dAAV vector contains the Rep and capsid gene coding sequences from AAV but lacks any of the inverted terminal repeat sequences. In the presence of helper virus infection, AAV Rep and capsid proteins are produced but the dAAV DNA is not replicated or packaged. Any of a number of dAAV vectors can be used as long as the vector chosen is capable of expressing the AAV Rep and capsid genes and is incapable of being packaged. Such dAAV vectors are well known in the art and will not be described in more detail here (see for example, Samulski et al. 1989). Preferably, the dAAV vector is pIM45 (McCarty et al. J. Virol. 65:2936–2945 1991). The helper virus may be any of a number of viruses known to promote productive viral infection of AAV in mammalian cells. Members of either the herpes or the adenovirus families can provide the necessary helper virus functions. Under some conditions vaccinia virus may be useful as a helper virus. Preferably, the helper virus is an adenovirus; most preferably, the helper virus is adenovirus 5. The host cells useful for preparation of the PCCE include any mammalian cells that are permissive for the replication of AAV, including but not limited to, HeLa cells or human 293 cells. Particularly useful are human cell lines that have been infected with a helper virus. Preferably the cell line used for the preparation of the PCCE is human 293 cells (Graham et al. 1977. J. Gen. Virol. 36:59–72).

The preparation of the PCCE is carried out by transfecting the host cell line with the dAAV vector and infecting with a helper virus by procedures that are well known in the art. Transfection may be performed by the DEAE-dextran method (McCutchen and Pagano, 1968, J. Natl. Cancer Inst. 41:351–357), the calcium phosphate procedure (Graham et al., 1973, J. Virol. 33:739–748) or by any other method known in the art, including but not limited to microinjection, lipofection, and electroporation. Transfection may be accomplished using helper virus infected cells, or may be performed simultaneously with, or prior to, viral infection. Infection with the helper virus is carried out by conventional methods. If adenovirus is used as helper virus, a desirable multiplicity of infection may be between about 5 and 10. Amounts of dAAV vector (and/or other vectors) used in transfection are approximately 0.2 to 10 µg of DNA per $10^6$ cells, but may vary among different DNA constructs and cell types.

Typically, for the preparation of the PCCE, the host cells grown to approximately 60% confluency are transfected with about 20 ug of a dAAV per 150 mm plate and infected with helper virus at a multiplicity of infection of approximately 5 to 10. The infected/transfected cells are harvested at approximately 48 hrs to several days after infection/transfection and washed first with cold phosphate buffered saline and then with a cold hypotonic solution. The washed cells are collected by centrifugation, resuspended in a small amount of hypotonic solution and incubated at 4° C. The cells are ruptured, for example, by dounce homogenization, and the NaCl concentration is raised to 0.2M. After incubation at 4° C., the suspension is cleared by centrifugation and the supernatant is dialyzed into a storage buffer and stored at low temperature, preferably −80° C. Suitable storage buffers for low temperature storage of macromolecules are well known in the art and typically contain a cryoprotectant, such as glycerol, in a buffered solution. Preferably, the storage buffer is 20 mM TrisCl (pH 7.4), 0.1 mM EDTA, 25 mM NaCl, 10% glycerol and 1 mM DTT.

Although the PCCE is most conveniently prepared by the methods described above, it will be apparent that suitable PCCE can be prepared in other ways, for example, by adding purified AAV Rep and capsid proteins to a cell extract prepared from helper virus infected cells or by using host cells that constitutively express the rep and/or cap proteins (see, for example, Yang et al., 1994 J. Virol. 68:4847). Alternatively, the cellular components essential for packaging present in the extract can be isolated by standard biochemical techniques and recombined with purified AAV Rep and capsid proteins to provide a complete packaging extract.

The in vitro packaging method of the present invention is carried out by combining the PCCE and appropriate DNA substrate and incubating under conditions to promote packaging. The conditions to promote packaging comprise suitable concentrations of $MgCl_2$, deoxyribonucleotide triphosphates, ribonucleotide triphosphates, ATP regenerating system and buffer. Optionally, following the incubation step, the in vitro packaged viral particles may be heated to inactivate any helper virus that might be present in the PCCE. Heat treatment also inactivates any cellular proteins that might associate non-specifically with the in vitro packaged particles. In vitro packaged AAV particles are heat stable (as are in vivo produced AAV virions). In one embodiment of the method of the present invention, the heat treated in vitro packaged particles are extracted with chloroform. In a second embodiment of the present invention, the chloroform extraction is omitted.

Typically, the incubation of the in vitro packaging method of the present invention is carried out as follows. An aliquot (approximately 0.5 volume of the final reaction solution) of the PCCE is brought to approximately 7 mM $MgCl_2$, approximately 30 mM Hepes buffer (pH 7.5), approximately 0.5 mM dithiothreitol or similar reducing agent, approximately 0.1 mM each dATP, dCTP, dGTP and dTTP, approximately 4 mM ATP, approximately 0.2 mM each CTP, UTP and GTP, approximately 40 mM creatine phosphate, approximately 37.5 ug/ml creatine kinase and approximately 0.1–100 ug/ml substrate DNA. The reaction is incubated at 37° C. for about 4 hrs. It will be apparent to one of ordinary skill in the art that some modification of these conditions is permissible and appropriate and can be readily determined by assaying the yield of infectious particles obtained. Following the incubation, the reaction may be optionally heated to remove any extraneous cellular protein that may be non-specifically associated with the AAV particles and to inactivate any residual helper virus. Typically, heating to about 55° C. for about 30 minutes is sufficient. If the production of chloroform-resistant particles is desired, the heat treated reaction is extracted several times with chloroform. Omission of the chloroform extraction generally yields a mixture of chloroform-sensitive and chloroform-resistant particles, depending on the particular substrate DNA packaged.

The in vitro packaging method of the present invention is useful for producing two types of in vitro packaged AAV particles, chloroform-resistant particles (CRPs) and chloroform-sensitive particles (CSPs). Both CRPs and CSPs of the present invention are capable of transferring the packaged substrate DNA to recipient cells. They differ in the structural requirements of the substrate DNA for the in vitro packaging reaction and in size as determined by sucrose gradient sedimentation velocity. CRPs and CSPs are prepared in an identical fashion according to the in vitro packaging method of the present invention described above except that for the preparation of CSPs the chloroform extraction step is omitted.

Chloroform-resistant particles are identical to in vivo packaged AAV particles by several criteria including density as measured by cesium chloride gradient centrifugation and resistance to treatment with chloroform, heat or DNase I. For production of CRPs, the substrate DNA should be no larger than about 120% of the size of wt AAV genome size. Preferably, the substrate DNA is between 50% and 110% of the size of wt AAV genome; most preferably, the substrate DNA is between 80% and 105 % of the size of the wt AAV genome. Additionally, the substrate for production of CRPs contains the intact AAV inverted terminal repeat sequences or the double-D sequence described in WO 9413788. Optimally, the substrate DNA for production of CRPs is either single-stranded or double-stranded replicative form (RF) DNA. RF-rAAV for use as a substrate for the in vitro packaging method of the present invention can be produced by techniques that are well known in the art (see, for example, Hermonat et al. 1984; Snyder et al., 1990 J. Virol. 64:6204–6213; and Hong et al., 1994 J. Virol. 68:2011–2015). Typically, RF-rAAV is prepared by co-transfection of mammalian host cells permissive for AAV replication with the rAAV plasmid DNA and a helper virus, such as adenovirus. The transfection is carried out by procedures similar to those described above. Depending on the particular AAV sequences present on the rAAV, any missing AAV functions that are essential for AAV replication and packaging functions can be supplied in trans by transfecting with a AAV helper plasmid containing the requisite AAV genes but lacking the TR sequences. Preferably, the AAV helper plasmid and the rAAV do not contain sequences in common in order to lessen the possibility of recombination to form wt AAV RF. Most preferably, the helper AAV plasmid is pIM45 (McCarty 1991). Other helper AAV plasmids are also suitable, for example, pAAV/Ad (Samulski et al., 1989) which contains the adenovirus 5 terminal sequences in place of the AAV TR, or pHIV rep (Antoni et al., 1991, J. Virol. 65:396–404). The RF-rAAV DNA may be isolated from the transfected cells by procedures that are well known in the art, such as a modified Hirt procedure (J. Mol. Biol. 26:365–369 1967). DNA isolated by these procedures is substantially free of other cellular and viral components. RF-rAAV may also by chemically or enzymatically synthesized (see Snyder et al 1993 J. Virol. 67:6096–6104) or may be made from circular plasmids containing the AAV TR and progate in bacteria (see Hong et al., 1994).

For the production of CSPs of the present invention, the substrate DNA is not limited by size or by the presence of AAV TR sequences. In vitro packaged substrate DNAs up to two-fold larger than the size of the wt AAV genome are efficiently transferred to and expressed in recipient mammalian cells. The size of the substrate DNA for the production of CSPs is limited only by the ability to manipulate large DNAs without damage. The substrate DNA for the production of CSPs may be between 50% and 500% of the size of wtAAV genome. Preferably the substrate DNA for the production of CSPs is between 100% and 200% of the size of the wt AAV genome. The substrate DNA for the production of CSPs need not contain any AAV sequences, in particular the substrate DNA need not contain the AAV TR sequences. However, inclusion of AAV TR sequences may be useful for efficient integration and rescue of the transferred substrate DNA following transduction. Finally, the substrate DNA for the production of CSPs need not be in the form of a AAV RF. Linear or circular plasmid DNA is suitable as substrate DNA for the production of CSPs. Suitable substrates include chemically or enzymatically synthesized DNAs.

The nature of the particular substrate DNA used for the in vitro packaging method of the present invention will depend primarily upon the particular genes or other DNA sequences desired to be transferred to the recipient cell. The substrate DNA is not limited to any particular genes, coding sequences, promoters or other DNA sequences other than those described above. Any gene or other recombinant DNA capable of expression or function in the mammalian recipient is suitable for inclusion in the substrate DNA. It may be desirable to incorporate a gene with a readily detectable product (known in the art as a marker, recorder, or reporter gene) as part of the substrate DNA although the invention is not limited to such constructs. Readily detectable reporter genes may produce either tumorigenic or non-tumorigenic products. Tumorigenic reporter genes may be utilized, but are less desirable due to their oncogenicity. Non-tumorigenic reporter genes would include, but are not limited to, β-galactosidase, neomycin phosphoro-transferase, chloramphenicol acetyltransferase, thymidine kinase, luciferase, β-glucuronidase, and xanthine-guanine phosphoribosyl transferase, to name but a few. Some examples of DNAs that have been transferred using in vivo packaged AAV particles include the bacterial neomycin phosphotransferase gene under the control of the SV40 early promoter (Hermonat and Muzyczka, 1984); the bacterial chloramphenicol acetyltransferase gene under the control of the AAV P40 promoter (Tratschin et al. 1984 Mol. Cell Biol. 4:2072–2081); human β-globin c-DNA (Ohi et al. 1990 Gene 89:279–282); and human thyrotropin (Wondisford et al. 1988 Mol. Endocrinol. 2:32–39). Other genes or coding sequences that are useful in combination with the method of the present invention are cytokines, such as GM-CSF, G-CSF, M-CSF; interleukins, such as IL-2, IL-3, IL-7, IL-13; nerve growth and neurotrophic factors, such as NGF, CNTF, BDNF; tyrosine hydrolase, dopa decarboxylase, factor XIII and factor IX. These and similar DNAs are suitable for transfer using in vitro packaged AAV particles. In addition, because the CSPs of the present invention may be prepared using substrate DNA that is larger than is possible for in vivo packaged AAV particles, there is less constraint on the size of the gene or other DNA sequence that can be transferred by the method of the present invention.

The titer of the in vitro packaged AAV particles can be determined by methods generally employed for determination of recombinant AAV viral titer for in vivo generated viral stocks. The particular method chosen will depend on the particular genes or other DNA carried by the substrate DNA. For example, if the substrate DNA carries the β-galactosidase gene (Lac Z), the titer may be estimated by measuring the frequency of expression of the β-galactosidase gene in the transductants. Alternatively, all rAAV titers can be determined by the infectious center assay (McLaughlin et al. 1988). Virus particle titers can be determined by dot blot assay or spectrophotometrically by methods that are well known in the art. Typically, the in vitro packaging method of the present invention provides infectious viral titers of at least $10^5$/ml. The particle titers are correspondingly at least $10^7$/ml (AAV infectivity ratio is typically 100:1).

The in vitro packaged AAV particles of the present invention may be used for transduction of recipient mammalian cells in an identical fashion to that employed for transduction using in vivo packaged AAV particles. By transduction is intended the transfer to and expression or function in recipient cells of substrate DNA. Such transduction procedures are well known in the art (see, for example McLaughlin et al. 1988; Hermonat and Muzyczka, 1984; Tratschen et al. 1985). Typically, the recipient mammalian cells may be infected with the in vitro packaged AAV particles without helper virus, particularly the packaged substrate DNA contains AAV TR sequences, resulting in a formation of a provirus. This is the method of choice particularly for transduction of living organisms, for example, animals. Alternatively, the recipient mammalian cells are coinfected with the in vitro packaged AAV particles and a helper virus.

The recipient mammalian cell may be any particular mammalian cell susceptible to infection by AAV, including but not limited to human, rabbit, simian, murine, bovine, canine, and simian. The recipient mammalian cells include primary cells, established cell lines, organized tissue and organisms. AAV has been shown to be capable of transducing, for example, murine and primate brain cells and murine, primate and rabbit lung cells.

Specific examples of the steps described above are set forth in the following examples. However, it will be apparent to one of ordinary skill in the art that many modifications are possible and that the examples are provided for purposes of illustration only and are not limiting of the invention unless so specified.

EXAMPLES

Example 1

Preparation of cell extracts containing AAV packaging components (PCCE)

Materials. Ribonucleotides, deoxyribonucleotides, creatine phosphate, creatine phosphate kinase, and aphidicolin were purchased from Sigma or Pharmacia. Protein G-Sepharose was from Pharmacia. Ascites preparations of the anti-Rep monoclonal antibodies anti-rep52/40 and anti-rep78/68 (Hunter and Samuiski, 1992, J. Virol. 66:317–324) were prepared by Rockland Inc and purified on protein G Sepharose prior to use. The Western detection kit, ECL, was purchased from Amersham and used as suggested by the manufacturer. Guinea pig anti-AAV capsid protein polyclonal antibody was provided by Dr. R. J. Samulski (University of North Carolina). Cationic liposomes was prepared and used as described (Gao, 1991 Biochem. Biophys. Res. Comm. 179:280–285). Restriction endonucleases were purchased from New England BioLabs.

293 cells were maintained in DMEM medium containing heat-inactivated calf serum and antibiotics (Graham et al. 1977 J. Gem Virol. 36:59–72). Only cells that had undergone fewer than 100 passages were used and they were plated one day prior to transfection or infection. Adenovirus 5 (obtained from ATCC) was prepared by conventional methods. The plasmid d163-87/45 was constructed by digesting pIM29+45, which has been renamed pIM45 (McCatry et al. 1991 J. Virol. 65:2936–2945), with ApaI and religating the resulting larger fragment. Plasmid pIM45 contains all of the AAV coding sequences but is missing the AAV terminal repeats. Plasmid d163-87/45 contains a 1103 base deletion (relative to pIM45) within the capsid coding region which causes a frameshift mutation (See FIG. 1).

Preparation of cell extracts. Ten 150 mm plates of 293 cells at approximately 60% confluency were transfected with 20 ug of plasmid DNA per plate using cationic liposomes (Gao 1991) and infected with adenovirus 5 at a multiplicity of infection (MOI) of 5. The cells were harvested at 48 h post infection and washed with 20 ml cold phosphate buffered saline (PBS) and then 10 ml cold hypotonic buffer (20 mM HEPES (pH7.4), 5 mM KCl, 1.5 mM MgCl$_2$, 1 mM DTT). The cell suspension was centrifuged and the cell pellet was resuspended in a final volume of 4.8 ml of hypotonic buffer and incubated on ice for 10 min. The cell suspension was dounce homogenized (20 strokes with a type B pestle) and 0.2 ml of 5M NaCl was added to raise the NaCl concentration to 0.2M. The suspension was incubated on ice for 1 h and the extract was cleared by centrifugation at 15,000×g for 20 min. After dialysis against a buffer containing 20 mM TrisCl (pH7.4), 0.1 mM EDTA, 25 mM NaCl, 10% glycerol, 1 mM DTT, the extract was stored at −80° C.

The AAV packaging extract was prepared from cells infected with adenovirus and transfected with pIM45 or the negative control plasmid d163-87/45. Previous work had demonstrated that the mutation in plasmid d163-87/45 was completely defective for packaging but viable for AAV DNA replication (Hermonat and Muzyczka, 1984). Finally, extracts were also made from cells that had been infected only with adenovirus.

Western analysis was carried out on samples of the extracts. Ten microliters of each cell extract was electrophoresed on 8–14% polyacrylamide gradient gels. Proteins were transferred to nitrocellulose membranes and the Rep and capsid proteins were detected with anti-Rep monoclonal antibody anti-rep52/40 and guinea pig anti-capsid polyclonal antibody, respectively. The western blots were visualized using an ECL kit following the manufacturer's protocol.

Figure 2:
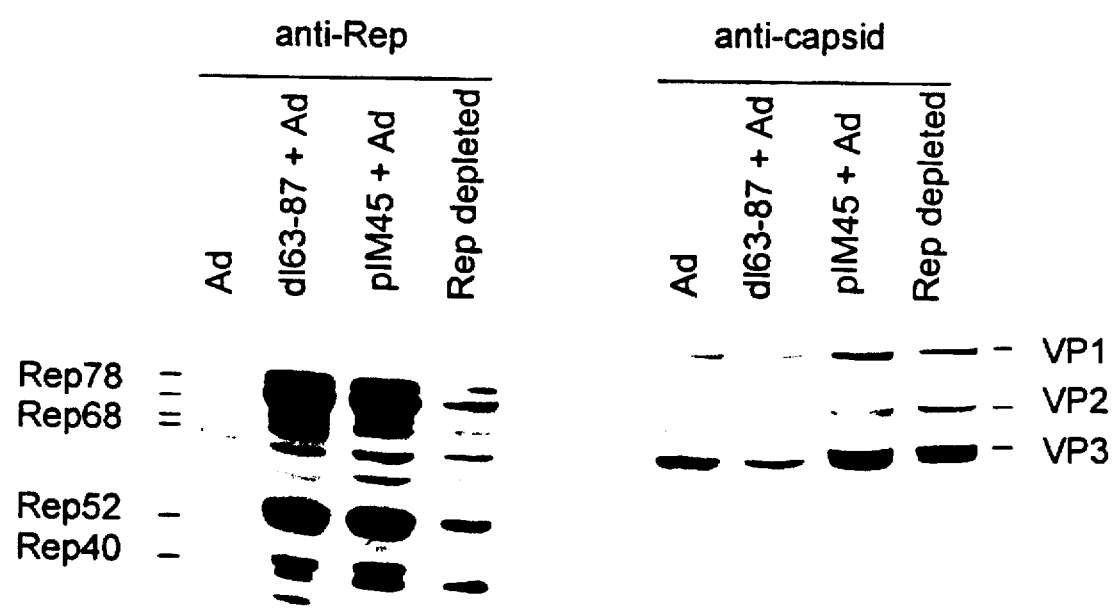
FIG. 2. Western analysis of in vitro packaging cell extracts. Extracts were prepared as described in Example 1 from 293 cells infected with adenovirus alone, or infected with adenovirus and transfected with either d163-87/45 or pIM45 plasmid DNA. Partial depletion of Rep proteins from pIM45+Ad extract was accomplished by incubating the extract with mouse monoclonal anti-Rep78/68 antibody coupled to protein G-beads. Ten µl of each extract was electrophoresed on a polyacrylamide gel transferred to a nitrocellular membrane and probed for Rep proteins (left panel) using the anti-Rep mouse monoclonal antibody which recognizes all four Rep proteins or guinea pig polyclonal anticapsid antibody which recognizes all three capsid proteins (right panel).

As expected, pIM45 derived extracts contained all of the AAV coded proteins: the nonstructural proteins Rep78, Rep68, Rep 52, and Rep 40; and the three AAV capsid proteins VP1, VP2, and VP3 (FIG. 2). In contrast, extracts prepared from d163-87/45 transfected cells did not have detectable levels of AAV capsid proteins but had normal levels of the Rep proteins. The absence of truncated capsid proteins in the d163-87/45 extract was presumably due either to the instability of the proteins or to the absence of the epitopes required for antibody recognition. Extracts prepared from cells infected with adenovirus alone contained neither Rep nor capsid proteins.

Example 2

Preparation of DNA substrate for the packaging reaction

Plasmids pTRLacZ and pAB11 (kindly supplied by Dr. R. J. Samulski, University of North Carolina) are recombinant AAV vectors which contain the E. coli β-galactosidase gene (LacZ) under the control of the cytomegalovirus (CMV) immediate early promoter (FIG. 1). The two plasmids differ only in that pAB11 is missing an internal PstI site and contains a nuclear localization signal in the coding sequence of its LacZ gene.

pTRLacZ contains the 3.7 KB BamHI/HindIII fragment carrying the LacZ coding region from pCH110 (from Pharmacia) ligated at the HindIII end to the 0.9 KB BamHI/HindIII CMV promoter fragment from pBS-CMV (from Pharmacia) and cloned into the BglII site of pTR.

pTR was constructed by stepwise ligation as follows. The 160 bp PstI/BglII fragment carrying the left AAV TR from plasmid dl3-94 (McLaughlin et al, 1988) was ligated to a 1270 bp Ad 2 fragment (stuffer fragment). The resulting 1430 bp fragment was ligated to a 50 bp synthetic DNA fragment, with BamHI and BglII compatible ends, containing the sequence for the SV40 early polyadenylation signal. The resulting 1480 bp fragment was ligated to another copy of the 160 bp PstI/BglII fragment containing the left AAV TR. The resulting 1640 bp fragment was digested with PstI, gel purified and ligated into the PstI site of pBR322.

pTRLacZ was chosen for the packaging experiments for two reasons. First, it could be easily distinguished from any contaminating wild type AAV virus. Second, it provided an easy method for measuring the efficiency of the in vitro packaging reaction. This was done by applying the products of the in vitro reaction to cells and then staining the infected cells for β-galactosidase activity.

For preparation of pTRLacZ replicative form DNA, 293 cells were cotransfected with 10 ug per 100 mm plate of pIM45 and pTRLacZ DNA (3:1) using cationic liposomes and infected with adenovirus at 5 MOI. Rescued and replicated AAV(TRlacZ) DNA was extracted 48 h later using the method of Hirt (J. Mol. Biol. 26:365–369 1967). The concentration of AAV(TRlacZ) DNA was determined by comparison with known amounts of AAV plasmid DNA following electrophoresis in an agarose gel and staining with ethidium bromide.

Example 3

In vitro packaging of substrate DNA

The complete in vitro packaging reaction contained in 30 ul: 30 mM Hepes (pH 7.5); 7 mM $MgCl_2$; 0.5 mM DTT; 0.1 mM each dATP, dGTP, dCTP and dTT; 4 mM ATP; 0.2 mM each CTP, GTP, and UTP; 40 mM creatine phosphate; 37.5 ug/ml creatine phosphokinase; 0.17 ug/ml of pTRLacZ RF DNA; and 15 ul of cell extract (PCCE) from Example 1. The reaction was incubated at 37° C. for 4 h. The products of the reaction were then incubated at 55° C. for 30 min and extracted with chloroform twice unless otherwise indicated. Additional in vitro packaging reaction were carried out using other DNA substrates in place of pTRLacZ RF (Table II).

The efficiency of the in vitro packaging reaction was assessed by infection of cells with aliquots of the packaged virus. The products of the packaging reaction were added to 293 cells in 96 well plates at $5 \times 10^4$ cells per well. The cells were coinfected with adenovirus 5 to enhance the transient expression of AAV transgenes and the cells were stained for beta-galactosidase at 48 h post infection using X-gal as described (Dhawan et al., 1991, Science 254:1509–1512).

The titer of wild type AAV was determined by the infectious center assay (McLaughlin et al. 1988). Aliquots of virus stocks were used to infect 293 cells in a 96 well plate at a density of $5 \times 10^4$ cells per well. The cells were coinfected with adenovirus 5 at an MOI of 5. After 30 hours of incubation at 37° C., the cells were trypsinized and transferred onto nylon membranes with a filtration device. The membranes were wet for 3 minutes on 3MM paper saturated with a solution containing 0.5N NaOH and 1.5M NaCl. This step was repeated once after the membranes were blotted dry. The membranes were neutralized with 1M TrisCl (pH7.5), 1.5M NaCl and heated in a microwave for 5 minutes. The membranes were hybridized with wild type AAV probe. Each spot on the membrane hybridizing to the probe represented one cell lytically infected by AAV.

When pTRLacZ DNA was incubated with the crude extract obtained from cells transfected with pIM45 and adenovirus, a significant number of the cells treated with the products of the reaction were capable of expressing the LacZ gene (Table I). This was not true of reactions incubated with extracts derived from cells transfected with dl63-87/45 plus adenovirus or from cells infected with adenovirus alone. Since the dl63-87/45 extract lacked only the capsid proteins (compared to the pIM45 extract), the transfer and expression of the TRLacZ DNA was being facilitated by some process that required AAV capsid proteins. Previous work with the pTRLacZ vector had suggested that the viral titer obtained by staining for β-galactosidase activity was approximately 20 fold lower than the titer of infectious virus as determined by the infectious center assay. Thus, the frequency of β-galactosidase transduction obtained from the products of the in vitro packaging reaction suggested that as much as $10^5$ infectious virus had been synthesized per ml of reaction mixture. Assuming a particle to infectivity ratio of 100:1, this would represent the production of $10^7$ AAV recombinant particles per ml of reaction.

Example 4

Determination of the Density of the in vitro packaged AAV(TRlacZ) particles

Since the density of the virus particle is a function of the protein and DNA content of the particle, we predicted that the density of the in vitro packaged AAV(TRLacZ) particles should be indistinguishable from wild type AAV virus. The density of the AAV virion particles was determined by a cesium chloride gradient centrifugation method. In vitro packaged AAV(TRLacZ) was added to 4 ml of cesium chloride solution with a final refractive index of 1.3720. The solution was centrifuged in an SW50.1 rotor at 40 krpm for 20 hr at 4° C. In vivo packaged wild type AAV was run in parallel CsCl gradient. Two hundred microliter fractions were taken from the top of the gradient and the refractive index of each fraction was determined. Fractions were then dialyzed against PBS and the titer of wild type AAV or AAV(TRlacZ) was determined by the infectious center assay or by staining for beta-galactosidase activity, respectively.

Figure 3:
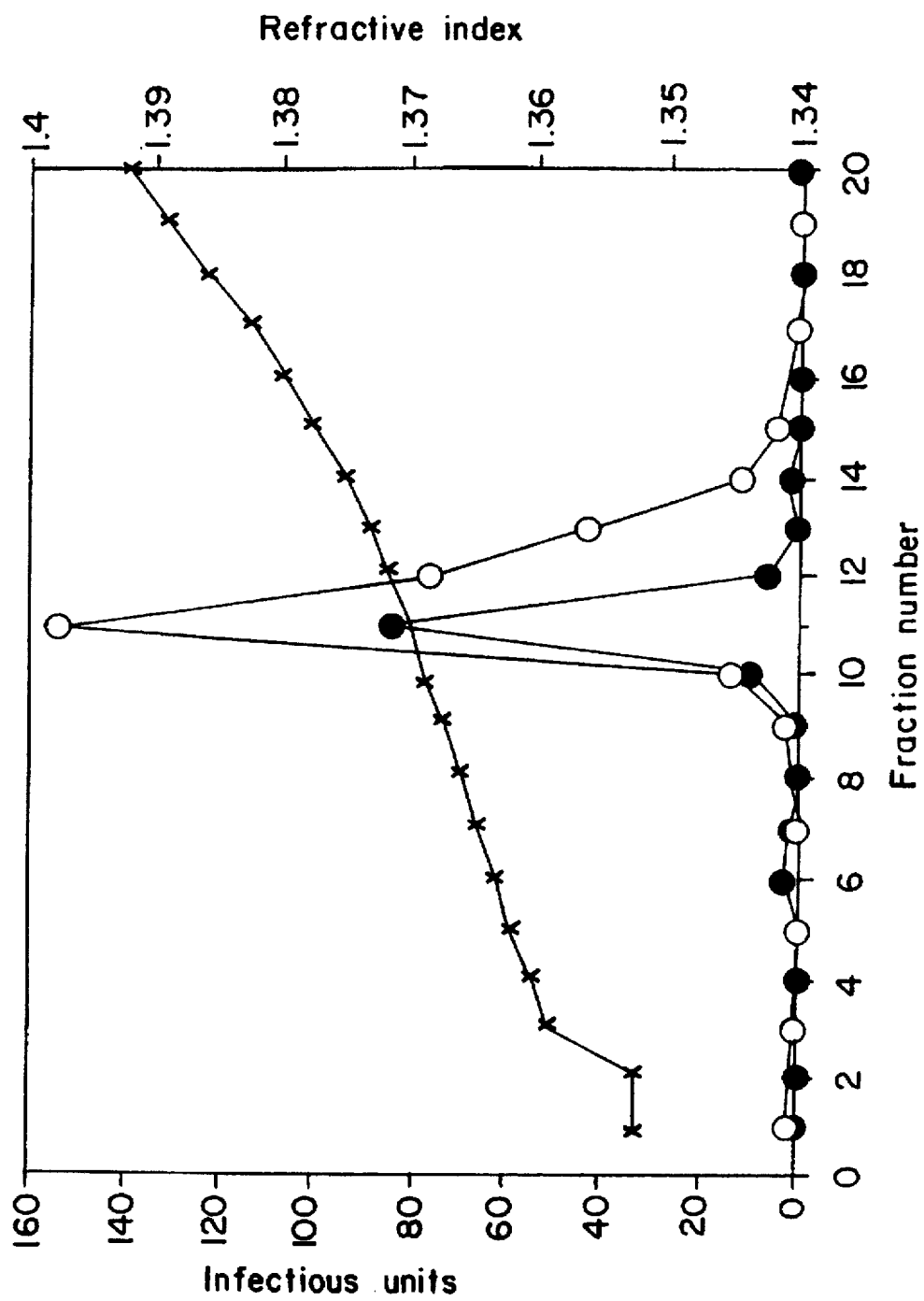
FIG. 3. Cesium Chloride Density gradient centrifugation of in vitro packaged pTRLacZ virus and wild type AAV packaged in vivo. In vitro packaged pTRLacZ virus and wild type AAV virus produced in vivo were centrifuged in parallel cesium chloride density gradients as described in Example 3. pTRLacZ (solid circles) virus was titered with the beta-galactosidase staining method; wild type AAV (open circles) was titered by the infectious center assay. Both virus preparations were heated at 55° C. for 30 minutes but not extracted with chloroform.
Figure 4:
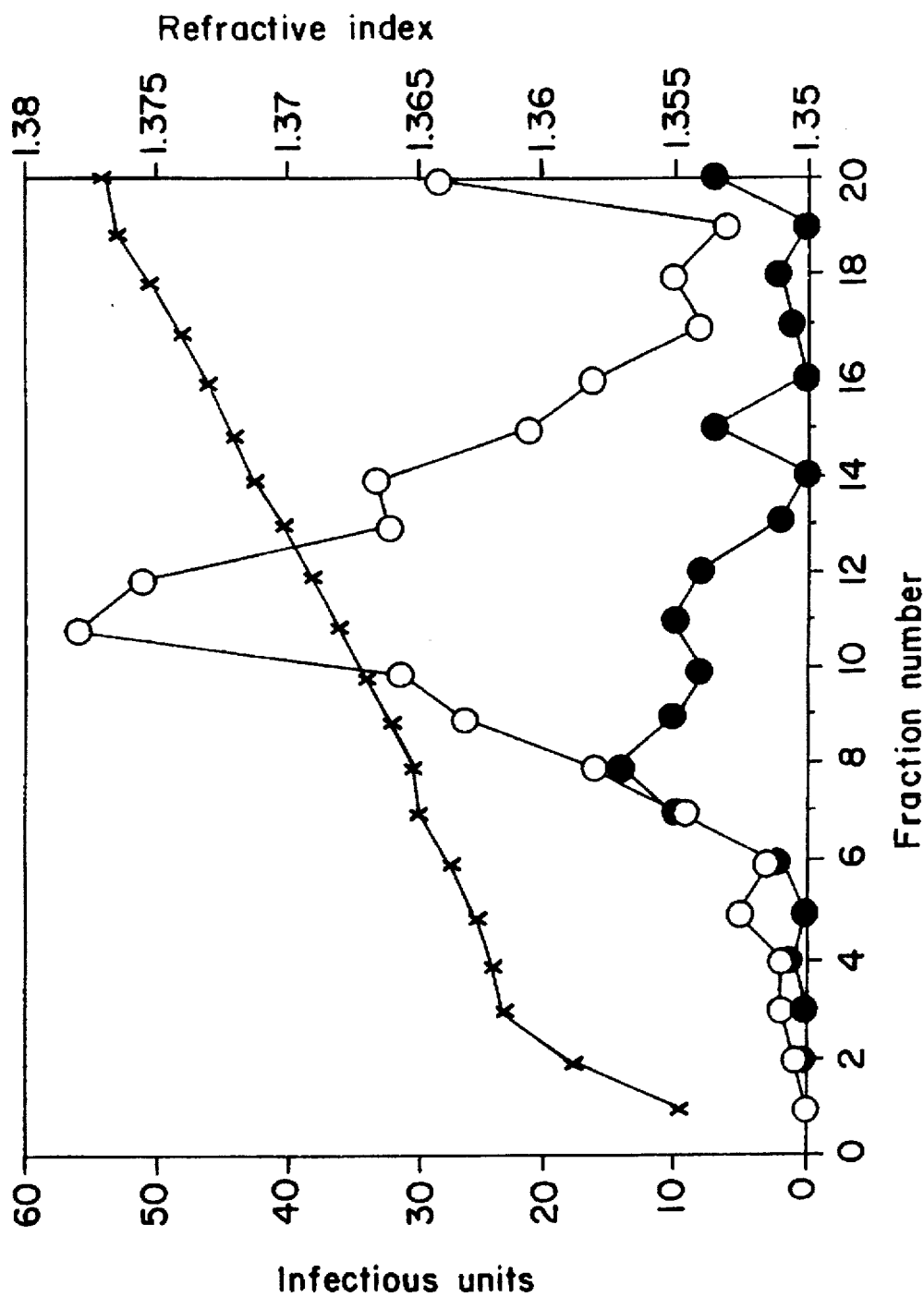
FIG. 4. Sucrose gradient centrifugation of in vivo packaged wtAAV and in vitro packaged AAV(TRLacZ). Peak fractions from the CsCl gradient were sedimented in 15–30% sucrose gradients. The virus was titered as in FIG. 3. pTRLacZ (solid circles); wtAAV (open circles); -X- refractive index.

In vitro synthesized particles had the same density as authentic wild type AAV. The pTRLacZ genome was nearly the same size as the wild type AAV genome (104% of wild type AAV). As shown in FIG. 3, both types of particles produced a single peak of activity, and the density of the two types of particles was virtually the same. Both the wild type and β gal particles had a peak refractive index of 1.3698, equivalent to a density of 1.38 g/ml.

Example 5

Structural Requirements for in vitro Packaging Substrate DNA

To determine whether the in vitro packaging reaction required an intact terminal repeat, single and double stranded RF substrates (prepared as described in Example 2) with substrates that either contained deletions within the terminal repeats or had additional sequences attached to each terminal repeat (Table II). The modified substrates were generated by digesting pTRLacZ plasmid DNA or pAB11 DNA with one of several restriction enzymes that cut within the terminal repeat or vector sequences of the plasmid but left the CMV and LacZ sequences intact (FIG. 1). In addition we examined the effect of chloroform extraction on the products of the reaction.

When the products were chloroform extracted, only the in vivo derived RF substrates which contained perfect terminal repeats were efficiently packaged (Table II, ds and ss RF DNA). No preference was seen for single stranded (ss) RF AAV(TRLacZ) DNA even though single stranded genomes are packaged in AAV particles. Substrates that contained plasmid vector sequences attached to the ends of the terminal repeats (BamH1 substrate), even those that contained only 23 additional bases attached to each end of the pTRLacZ genome (PstI substrate), were not efficiently packaged (Table II and FIG. 1). These were approximately 8 fold less efficient in transferring the β-galactosidase gene to cultured cells. Similarly, substrates which had 46 bp (Sinai substrate) or 121 bp (SmaI substrate) deleted from the ends of the 145 bp terminal repeats were also poorly packaged.

In contrast, in vitro reaction products that were not treated with chloroform prior to testing for β-gal transfer activity behaved differently (Table II). First, the products contained approximately twice the amount of transfer activity that was seen with chloroform extracted product, suggesting that a significant amount of β-gal transfer activity was due to particles that were not stable in chloroform. Furthermore, the additional β-gal transfer activity was largely insensitive to the size of the DNA substrate. The plasmid substrate digested with BamH was approximately twice the size of the wild type AAV genome but was still efficiently transferred.

Surprisingly, the additional β-gal transfer activity did not require an intact AAV terminal repeat sequence; substrates digested with either MscI or SmaI were efficiently transferred. Finally, the chloroform sensitive β-gal transfer product was sensitive to digestion with DNase I.

Example 6

Requirement for Rep proteins and certain cofactors

In vitro AAV DNA replication requires the presence of either Rep78 or Rep68 (Im et al. 1989 J. Virol. 63:3095-3104; Im et at., 1990 Cell 61:447-457; Snyder et al. 1993 J. Virol. 67:6090-6104) and AAV DNA synthesis is inhibited by aphidicolin. To determine whether Rep78 or Rep 68 were required for in vitro packaging, the Rep proteins were depleted from the packaging extract by immunoprecipitation of the extract with anti-78/68 monoclonal antibody conjugated to protein-G Sepharose beads (Harlow and Lane, 1988, in Antibodies: a Laboratory Manual, Cold Spring Harbor Laboratories, pp. 522-523). To immunoprecipitate Rep proteins, 3 volumes of cell extract were incubated twice with 1 volume of anti-rep78/68-protein G beads at 4° C. for 1 h with rocking. This procedure was successful in reducing the Rep78 and 68 concentration by approximately 10 fold without significantly affecting the concentration of capsid protein in the extract (FIG. 2). Rep52 and –40, which were not recognized by the anti Rep78/68 antibody, were also partially depleted possibly due to their interaction with the larger Rep proteins. When the depleted extract was tested for packaging activity it was found to be significantly reduced in activity (approximately 4 fold) compared to the complete extract (Table III). Addition of 10 ug/ml aphidicolin to the reactions containing the complete extract reduced activity approximately 9 fold. Finally, addition of aphidicolin to the depleted extract reduced the packaging activity even further, approximately 20 fold. We also measured the level of DNA synthesis under the conditions of reduced Rep concentration and aphidocolin treatment and found that the level of DNA synthesis was reduced to approximately the same extent as the level of in vitro packaging (data not shown). These results indicate that the presence of one or more of the Rep proteins and active DNA synthesis was required for in vitro AAV packaging.

The divalent cation $Mg^{++}$ and ATP were found to be essential for packaging activity (Table IV). This was true for both CRP or CSP. Omission of Mg ion completely eliminated packaging activity, while omission of ATP or the ATP regenerating system, creatine phosphate and creatine phosphokinase, severely inhibited the packaging reaction (approximately 20 fold). The residual activity seen in the absence of ATP or the regenerating system presumably reflects the fact that the cell free packaging extract contained substantial amounts of ATP. Since both Mg and ATP are necessary for AAV DNA replication, the requirement for these cofactors was not surprising. This also probably explains the modest decrease in activity seen when the four deoxynucleoside triphosphates were omitted from the reaction (approximately 40%). Again, although the deoxynucleoside triphosphates are essential for DNA replication, the cell free packaging extract is likely to have contained substantial amounts of these nucleotides. The reaction was also partially dependent on the presence of the other three ribonucleoside triphosphates, UTP, CTP and GTP.

Example 7

Sucrose gradient centrifugation of wtAAV and in vitro packaged AAV(TRLacZ).

A linear gradient of from 15% to 30% (wt/wt) sucrose was prepared in 10 mMTrisCl (pH8.8). Peak fractions form the CsCl gradient were dialyzed against PBS, adjusted to 100 ul and loaded on top of the sucrose gradients. The gradients were centrifuged for 2.5 hours at 20° C. at 110,000 g. Fractions were collected, dialyzed against PBS and analyzed for wt AAV or AAV(LacZ) as described for the CsCl gradients.

In general, the sedimentation profiles of the two particle preparations was similar. Both contained species that sedimented at the position of mature 110S AAV particles. In addition, both preparations contained material that sedimented with either lower or higher sedimentation coefficients. The higher molecular weight species are likely to be aggregates of more than one AAV virus particle. The lower molecular weight species may be a packaging intermediate similar to the one identified by Myers and Carter in vivo. This group reported a potential intermediate during AAV packaging that had approximately the same density as mature AAV virus particles but had a sedimentation coefficient in sucrose gradients of 66S as opposed to 110S for the mature particle. The 66S particle reported by Myers and Carter appeared to have a complete AAV genome and was sensitive to DNaseI.

TABLE I

Capsid protein dependent in vitro packaging of substrate DNA. pTRLacZ replicative form DNA prepared as described in Example 2 was packaged using the extracts indicated below. The products of the reaction were extracted with chloroform and heated at 55° C. for 30 minutes. The yield of infectious units per 30 μl reaction was determined by infection and expression of the transgene in 293 cells using X-gal staining.

|   | number of blue cells | | |
|---|---|---|---|
| extract | expt. 1 | expt. 2 | expt. 3 |
| Ad | 0 | 0 | 0 |
| dl63 – 87/45 + Ad | 0 | 0 | 0 |
| pIM45 + Ad | 192 | 206 | 116 |

TABLE II

Substrate requirements for in vitro packaging. Various DNA substrates described in the text and FIG. 1 were packaged in vitro in the standard 30 μl reaction. The products were tested for β-galactosidase transduction either before or after treatment with chloroform. The products of the reaction were heated at 55° C. for 30 minutes. Shown are the number of blue cells produced by the products of each 30 μl reaction.

|   | number of blue cells | |
|---|---|---|
| DNA substrate | + chloroform | – chloroform |
| ds RF DNA | 120 | 300 |
| ss RF DNA | 178 | ND |
| PstI pAB11 | 15 | 288 |
| SmaI pTRLacZ | 20 | 172 |
| MscI TRLacZ | 8 | 116 |
| BamH1 pTRLacZ | 14 | 192 |

TABLE III

Dependence of in vitro packaging on Rep and DNA synthesis. pTRLacZ substrate was incubated with the indicated extract in the presence or absence of 10 μg/ml of aphidicolin. The products of the reaction were heat treated and extracted with chloroform.

| extract | aphidicolin | number of blue cells |
|---|---|---|
| pIM45 | – | 120 |
| pIM45 | + | 13 |
| Rep depleted | – | 29 |
| Rep depleted | + | 6 |

TABLE IV

Cofactor Requirements for in vitro packaging. AAV (TRlacZ) DNA was packaged under conditions in which one or more components were omitted. The products of the reactions were heated to 55° C. for 30 minutes and extracted with chloroform. Infectious units yielded were determined by infection and expression of the transgene in 293 cells.

| reaction conditions | number of blue cells |
|---|---|
| complete | 199 |
| −Mg++ | 0 |
| −GTP, CTP, UTP | 123 |
| −dNTPs | 120 |
| −ATP | 16 |
| −CP, CPK* | 14 |
| −ATP, CP, CPK | 10 |

*CP is creatine phosphate; CPK is creatine phosphokinase.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for in vitro packaging of a DNA substrate into AAV particles that transduce a recipient mammalian cell comprising the steps of:
   (a) transfecting a mammalian host cell culture permissive for AAV replication with a dAAV vector containing AAV capsid and Rep gene coding sequences;
   (b) infecting said host cell culture with a helper virus;
   (c) after said transfecting and said infecting, preparing an extract free of DNA from the transfected cell culture;
   (d) combining said extract with said DNA substrate; and,
   (e) incubating said extract under conditions to promote packaging of said DNA substrate.

2. The method of claim 1 comprising in addition, after said incubating step, the step of heating said extract at sufficient temperature for sufficient time to inactivate the helper virus.

3. The method of claim 2 comprising in addition, after said heating step, the step of extracting said extract with chloroform.

4. The method of claim 1 wherein said DNA substrate contains AAV terminal repeat sequences.

5. The method of claim 1 wherein said DNA substrate contains one or more genes or coding sequences selected from the group consisting of GM-CSF, G-CSF, M-CSF, IL-2, IL-3, IL-7, IL-13, NGF, CNTF, BDNF, tyrosine hydrolase, dopa decarboxylase, factor XIII and factor IX.

6. The method of claim 1 wherein said dAAV vector is pIM45.

7. The method of claim 1 wherein said helper virus is an adenovirus.

8. The method of claim 7 wherein said helper virus is adenovirus 5.

9. The method of claim 1 wherein the mammalian host cell culture is a human cell culture.

10. The method of claim 9 wherein said mammalian host cell culture is human 293 cells.

11. The method of claim 1 wherein the conditions to promote packaging comprise:
    about 7 mM MgCl$_2$; about 0.1 mM each of dATP, dCTP, dGTP and dTTP; about 4 mM ATP; about 0.2 mM each of CTP, UTP and GTP; about 40 mM creatine phosphate; about 37.5 ug/ml creatine phosphokinase; about 0.10 to 100 ug/ml substrate DNA; about 0.5 volumes of said extract; and about 30 mM Hepes buffer at about pH 7.5.

12. Chloroform sensitive AAV particles that transduce a recipient mammalian cell prepared by the method comprising the steps of:
    (a) transfecting a mammalian host cell culture permissive for AAV replication with a dAAV vector containing AAV capsid and Rep gene coding sequences;
    (b) infecting said host cell culture with a helper virus;
    (c) after said transfecting and said infecting, preparing an extract free of DNA from the transfected cell culture;
    (d) combining said extract with a DNA substrate; and,
    (e) incubating said extract under conditions to promote packaging of said substrate DNA.

13. Chloroform sensitive AAV particles that transduce a recipient mammalian cell prepared by the method comprising the steps of:
    (a) transfecting a mammalian host cell culture permissive for AAV replication with a dAAV vector containing AAV capsid and Rep gene coding sequences;
    (b) infecting said host cell culture with a helper virus;
    (c) after said transfecting and said infecting, preparing an extract free of DNA from the transfected cell culture;
    (d) combining said extract with a DNA substrate; and,
    (e) incubating said extract under conditions to promote packaging of said substrate DNA; and
    (f) heating said extract at sufficient temperature for sufficient time to inactivate the helper virus.

14. A method for transducing a recipient mammalian cell, said method comprising:
    infecting said recipient mammalian cell with the AAV particles of claim 12.

15. A method for transducing a recipient mammalian cell, said method comprising:
    infecting said recipient mammalian cell with the AAV particles of claim 13.

16. The method of claim 15 wherein said recipient mammalian cell is selected from the group consisting of primary cells, cell lines, tissue and organisms.

17. A method for preparing a composition that packages in vitro a DNA substrate into AAV particles that transduce a recipient mammalian cell, said method comprising:
    (a) transfecting a mammalian host cell culture permissive for AAV replication with a dAAV vector containing AAV capsid and Rep gene coding sequences;
    (b) infecting said host cell culture with a helper virus;
    (c) after said transfecting and said infecting, preparing an extract free of DNA from the transfected cell culture.

18. The composition prepared by the method of claim 17.

19. The method of claim 1 wherein said DNA substrate comprises at least the most inward 24 nucleotides of an AAV terminal repeat.

* * * * *